United States Patent [19]

Horwath et al.

[11] 4,442,207

[45] Apr. 10, 1984

[54] PROCESS FOR PRODUCTION OF GLUCOSONE

[75] Inventors: Robert O. Horwath, Westport; Osama O. Ibrahim, Brookfield, both of Conn.

[73] Assignee: Nabisco Brands, Inc., Parsippany, N.J.

[21] Appl. No.: 393,850

[22] Filed: Jun. 30, 1982

[51] Int. Cl.³ .................. C12P 19/02; C12N 9/04; C12R 1/645
[52] U.S. Cl. .................. 435/105; 435/190; 435/911
[58] Field of Search .................. 435/105, 190

[56] References Cited

U.S. PATENT DOCUMENTS

| | | | |
|---|---|---|---|
| 4,246,347 | 1/1981 | Neidleman et al. | 435/105 |
| 4,321,323 | 3/1982 | Maselli et al. | 435/105 |
| 4,321,324 | 3/1982 | Maselli et al. | 435/105 |

Primary Examiner—Lionel M. Shapiro
Attorney, Agent, or Firm—R. Kornutik

[57] ABSTRACT

Glucose-2-oxidase activity is produced by cultivating certain fungi of the Basidiomycetes class and the enzyme is employed in the oxidation of glucose to glucosone which can be converted to fructose.

8 Claims, 1 Drawing Figure

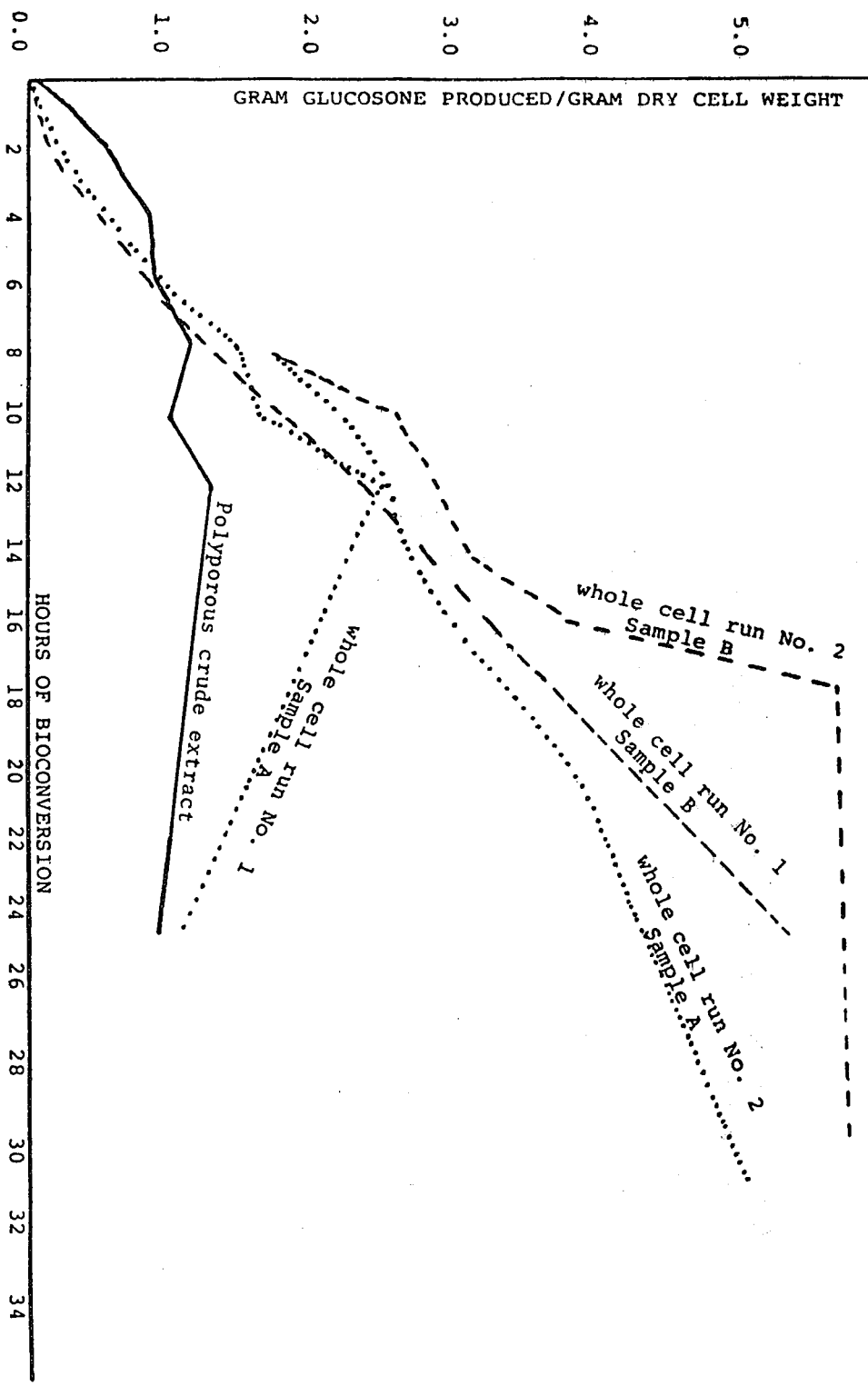

PROCESS FOR PRODUCTION OF GLUCOSONE

BACKGROUND OF THE INVENTION

This invention relates to enzymatic processes for converting glucose (dextrose) to glucosone which can be converted to fructose.

Most food grade glucose is provided as an enzymatic hydrolysate of corn starch, i.e., the corn syrup of commerce. Glucose is generally rated at being 60 to 80% as sweet as sucrose and therefore sells at a correspondingly lower price. It has long been known to isomerize glucose to fructose which is even sweeter than sucrose employing an enzyme having glucose isomerase activity, preferably one which has been immobilized upon an inert support such as diethylaminoethyl-cellulose, porous glass or chitin. The isomerization of glucose provides an equilibrium mixture typically containing 42–50% fructose and is referred to as high fructose corn syrup (HFCS).

Recently, it has been proposed to achieve substantially complete conversion of glucose to fructose by first enzymatically converting glucose to glucosone and thereafter chemically reducing the glucosone to fructose. Thus, in accordance with U.S. Pat. No. 4,246,347, the disclosure of which is incorporated by reference herein, at least about ninety-five percent of D-glucose in aqueous solution is enzymatically oxidized to D-glucosone employing an enzyme having glucose-2-oxidase activity, preferably one obtained from *Polyporus obtusus* or *Aspergillus oryzae*, while removing or utilizing co-produced hydrogen peroxide, the D-glucosone being thereafter hydrogenated to D-fructose. As is known in the art the glucose-2-oxidase obtained from *Polyporus obtusus*, the preferred organism up to the present, is employed in the form of a cell-free extract, primarily because only low enzyme activity is obtained when mycelia of this organism are used as the source of the enzyme.

These conversions, D-glucose to D-glucosone and D-glucosone to D-fructose, can be regarded as proceeding in accordance with the following equations:

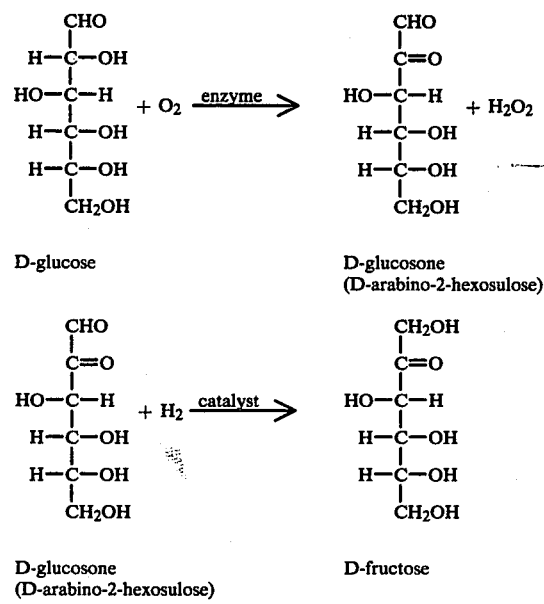

SUMMARY OF THE INVENTION

It has now been discovered that certain organisms of the Basidiomycetes class of fungi produce substantial quantities of glucose-2-oxidase and the mycelia of these organisms can be employed directly as a source of the enzyme in enzymatic conversion of glucose to glucosone. The organisms of the present invention are characterized in that substantially all of the glucose-2-oxidase activity is available on exposure to aqueous glucose substrates without disruption of the fungus. Accordingly, the high levels of enzyme attainable with the present fungi as well as the ready availability of the enzyme in the mycelia of these fungi makes these organisms more amenable to use in commercial production of glucosone, and thereafter other useful products such as fructose. Thus, in contrast with Polyporus fungi, the ability of the present fungi to provide glucose-2-oxidase at available high levels from the respective mycelia permits use of the mycelia in the enzymatic conversion reaction mixture without the necessity of disrupting the mycelia, i.e. without having to disrupt the mycelia as by sonic treatment or chemical lysing. In addition, the mycelia also provide enzymes, e.g. catalase and peroxidase, which destroy hydrogen peroxide, obviating the need for added chemical reactants or enzymes which would be required when cell free extracts are used.

Further, the present fungi possess substantially greater glucose-2-oxidase activity than the preferred *P. obtusus* and these include over twenty species of fungi of the Basidiomycetes class which have not been specifically identified as to the species to which they properly belong. These organisms produce at least about 3–5 times as much glucose-2-oxidase activity as *P. obtusus*.

Two particularly useful organisms which are species of fungi belonging to the Basidiomycetes class have been deposited with the National Regional Research Laboratory where they were assigned the accession numbers NRRL 15093 and NRRL 15094.

In addition to the aforementioned microorganisms, the present invention contemplates the use of mutants and variants thereof as well as genetically transformed microorganisms derived therefrom by introduction of the respective glucose-2-oxidase genes into other microorganisms including mesophilic and thermophilic microorganisms. Of particular importance are those genetically transformed microorganisms produced by introduction of mutated glucose-2-oxidase genes into preferably thermophilic microorganisms. The mutated glucose-2-oxidase genes selected for such use are those which provide glucose-2-oxidase of improved properties such as higher thermal stability. Such genes can be prepared by the usual techniques used form mutation of microorganisms such as irradiation or chemical means. For example, isolated glucose-2-oxidase genes which produce glucose-2-oxidase of moderate thermal stability, on in vitro mutagenesis will undergo mutation, and selection of the appropriate mutated genes is accomplished by reintroduction of the mutated gene into either the parent or other organism, preferably a thermophilic organism followed by replication of the organism and testing of the thermal stability of the resulting glucose-2-oxidase. In a similar manner, other improved properties of the enzyme can be tested.

The present invention provides higher enzyme activity than previously available from known fungi. In addition the use of the fungus mycelia avoids the necessity of forming cell-free extracts and also permits re-use of the same mycelia until the level of activity becomes uneconomical when the mycelia can be discarded. Further, the need for added chemicals or enzymes to destroy co-produced peroxide is obviated due to the presence of hydrogen-peroxide destroying enzymes in the fungus mycelia.

BRIEF DESCRIPTION OF THE DRAWING

The accompanying FIGURE is a graph showing the bioconversion of glucose to glucosone as a function of bioconversion time.

DESCRIPTION OF THE PREFERRED EMBODIMENTS

The glucose which is converted to glucosone in accordance with the present invention can be derived from any of the known sources for this sugar. For reasons of economy, the glucose used herein will usually be derived from the hydrolysis of cellulose or starch employing acid and/or enzyme, preferably the latter, in accordance with known procedures. Glucose obtained in this way will typically contain minor quantities of polysaccharides, sugar oligomers, etc., depending upon the carbohydrate source employed and the hydrolysis methods utilized. Cereal grains such as corn, milo, wheat, rye, and the like, and amylaceous roots and tubers such as potatoes, yams, carrots, cassava (manioc), and the like, are excellent sources of starch for conversion to the glucose starting material of this invention. In the United States, corn starch is especially preferred due to its comparatively low cost and ready availability. Since the production of food grade glucose favors the use of enzymatic starch hydrolysis procedures, such procedures are preferred herein. Enzyme hydrolysis methods are described in U.S. Pat. Nos. 4,017,363, 3,912,590, 3,922,196, 3,922,197-201 and 4,284,722, the disclosures of which are incorporated by reference herein. Glucose can be isomerized to fructose in accordance with the present invention employing any of the known procedures, including contacting glucose solutions with whole cells, or passing the solutions through a bed containing bound, or immobilized, glucose isomerase. Materials and procedures used for the immobilization of enzymes are well known and are described in a number of plublications including Wang, et al., *Fermentation & Enzyme Technology*, John Wiley & Sons, Inc., New York (1979), pp. 318–338 and Kirk Othmer, *Encyclopedia of Chemical Technology*, 3rd Ed., John Wiley & Sons, Inc., New York, (1980) Vol. 9, pp. 148–172, the disclosure of which are incorporated by reference herein.

The conversion of glucose to glucosone in accordance with this invention is advantageously carried out upon an aqueous solution of glucose, e.g., one containing from about 1 percent to about 30 percent, and preferably from about 3 percent to about 9 percent, by weight of glucose. It is further advantageous to conduct the conversion in the presence of fluoride ion, e.g., provided by sodium fluoride or calcium fluoride, as this is known from Volc, et al., "Glucose-2-Oxidase Activity and Accumulation of D-arabino-2-Hexosulose in Cultures of the *Basidiomycete Oudemansiella mucida*" 23 Folia Microbiol 292–298 (1978) to have a stimulating influence on the activity of the enzyme. When using mycelia of the selected fungus, amounts ranging from about one percent to about 10% percent mycelial dry weight by weight of glucose generally provide good results. Although not preferred, for reasons advanced hereinbefore, the same quantity of whole cells can be homogenized and centrifuged to provide a cell-free supernatant having glucose-2-oxidase activity which can then be used to achieve conversion of glucose to glucosone, either as free enzyme or in immobilized form. Materials and procedures used for the immobilization of enzymes are well known and are described in a number of publications including Wang, et al., *Fermentation & Enzyme Technology*, John Wiley & Sons, Inc., New York (1979), pp. 318–338, and Kirk-Othmer, *Encyclopedia of Chemical Technology*, 3rd Ed., John Wiley & Sons, Inc., New York, (1980) Vol. 9, pp. 148–172, the disclosures of which are incorporated by reference herein. Ordinarily, the duration of the enzyme reaction will be until substantially all of the original glucose is converted to glucosone, a factor which will be influenced in accordance with the precise procedures followed including whether co-produced hydrogen peroxide is removed from the reaction medium or not. Thus, in accordance with the mass law, removal of co-produced hydrogen peroxide, either by its enzymatic or chemical destruction or its removal or utilization immediately as it is formed, will shift the equilibrium of the reaction in favor of more rapid and complete conversion of glucose to glucosone. Other factors influencing the rate of conversion include pH and temperature, optimum levels of which can be established for a given system employing known and simple procedures. While glucose-2-oxidase remains active throughout a fairly broad range of pH and temperature, it is preferred to conduct the conversion of glucose to glucosone employing whole cells of the mycelia while maintaining a pH of from about 4.0 to about 8.5 and especially about neutral pH and at a temperature of from about 20° C. to about 60° C. and especially from about 30° C. to about 40° C. It is, of course, within the scope of this invention to convert only a part of the starting glucose to glucosone, in which case on hydrogenation a mixture of sorbitol and fructose will be obtained. The mixture can then be separated by known methods to obtain the respective products.

The conversion of glucose to glucosone requires oxygen which can be supplied as oxygen alone or oxygen in admixture with other gases such as air. The use of increased pressure of air (up to 15 pounds/in$^2$) is helpful. In steady-state operation, if the co-produced hydrogen peroxide is destroyed in situ upon its formation, e.g., by decomposition catalyzed by the enzyme catalase or by platinum, silver or the like, the resulting oxygen can partially satisfy the needs of the conversion reaction.

It is further contemplated herein to utilize the co-produced hydrogen peroxide in the manufacture of epoxide and/or glycol in the manner described in U.S. Pat. Nos. 4,247,641 and 4,284,723. In an improvement of the process of these patents, U.S. Pat. No. 4,321,324 the contents of which are incorporated by reference herein, discloses the enzymatic conversion of glucose to glucosone in a first zone with co-produced hydrogen peroxide being recovered from said zone through a semipermeable membrane which is permeable only to compounds of molecular weight of less than about 100 into a second zone wherein reaction of the hydrogen peroxide with olefin takes place to provide an oxygenated product, for example, alkylene halohydrin when a source of halogen anion and chloroperoxidase is present in said second zone. As disclosed, in U.S. Pat. No. 4,321,323 the contents of which are incorporated by reference herein, the use of such a semi-permeable membrane is useful per se as a means for removing hydrogen peroxide from the medium in which bioconversion takes place. It is particularly advantageous to employ a hollow-fiber semi-permeable membrane wherein glucose-2-oxidase is immobilized in or on the interior wall of the membrane in accordance with procedures described in Kirk-Othmer, *Encyclopedia of Chemical Technology*, 3rd Ed., John Wiley & Sons, Inc., New York (1980) vol. 9, pp. 148-172 and vol. 12, pp. 492-517, the disclosure of which is incorporated by reference herein, and other reference works.

Product glucosone can be converted to fructose employing any one of several enzymatic or chemical methods. Enzymatic conversion can be achieved with reductase as described in Kieslich, ed., *Microbial Transformation of Non-Steriod Cyclic Compounds*, Georg Threme Publishers, Stuttgart (1976), pp. 279-280, the contents of which are incorporated by reference herein. Chemical conversion can be achieved by classical hydrogenation techniques as described in U.S. Pat. No. 4,246,347, supra.

Alternatively, the glucosone product can be enzymatically oxidized using glucose-1-oxidase to 2-ketogluconic acid for example, as described in the scientific literature, e.g A Sols and G. de la Fuente, Rev. Espan. Fisial 13, 231 (1957). Any unreacted glucose which may be present in the isomerization reaction mixture will be converted to gluconic acid. A variety of microorganisms are known to produce glucose-1-oxidase and can be used to produce this enzyme which is also available commercially.

By way of illustrating the use of the present Basidiomucetes species to effect the conversion of glucose to glucosone in accordance with the present invention and to demonstrate the superiority of this microorganism for such conversion compared to *Polyporus obtusus*, a glucose-2-oxidase source preferred in the process of U.S. Pat. No. 4,246,347, the following experimental runs employing whole cells of each organism were carried out:

I. Materials and Procedures

A. Culture Maintenance: After incubating the cultures on malt agar slants for 7 days at 30° C., the isolates were inoculated into shaker flasks or maintained under refrigeration (about 20° C.).

B. Shake Flask Propagation: Inoculation medium was made up as follows:

| Ingredient | % By Weight |
|---|---|
| Cornsteep liquor | 2.0 (d.b.) |
| KH$_2$PO$_4$ | 0.1 |
| MgSO$_4$.7H$_2$O | 0.15 |
| Agar | 0.4 |
| adjust pH to 6.5 | |

80 Ml aliquots of the above medium were placed in 500 ml Erlenmyer flasks together with 20 ml of a 25% glucose solution (sterilized) for the inoculum fermentation. Production flasks were similarly charged except no agar was added.

First Stage (test tube) Propagation

In a sterile hood, approximately one half of the mycelia from a slant is transferred with a metal loop to a test tube with 10 ml of the inoculation medium and about six 3-mm glass beads (sterile). The tubes are vortexed for 30-60 seconds or until the mycelia are dispersed. The tubes are then placed on a G-50 shaker at 200 rpm, 30° C., for 7 days.

Second stage (inoculum) Propagation

After 7 days, 5 ml are transferred to a 500 ml Erlenmeyer shake flask, and 1 ml is transferred into brain heart infusion to check sterility. These inoculation flasks are placed on a G-50 shaker at 200 rpm, 30° C., for 7 days.

Third stage (production) Propagation

After 7 days, 5 ml are transferred from the inoculation flask to several fermentation flasks. The fermentation flasks are placed on the G-50 shaker at 200 rpm, 30° C., for 9 days.

C. Harvesting Cell Biomass: After the 9-day incubation period, the pH of each shake flask was measured; the cell biomass was filtered and washed twice with pH 7.0 phosphate buffer. After the second filtration, the harvested cell biomass from each culture was weighed and frozen for bioconversion.

D. Whole-cell Bioconversion: (under sterile conditions) Approximately 1 gram wet weight cells is placed into a 300 ml baffled flask containing 50 ml of glucose phosphate buffer (1% glucose added to the phosphate buffer w/v) and the suspension made 0.02 M in NaF. The flask is placed on the G-50 shaker at 200 rpm, and samples are taken at 6, 12, and 24 hours by aseptically transferring 2 ml from the bioconversion flask to 15 ml Corning centrifuge tubes. The samples are centrifuged for 5 min. then, 1 ml is removed and passed through a Sep-Pak C$_{18}$ cartridge (Waters Associates, Milford Ma.) following which the filtrates were analyzed by high pressure liquid chromatography (HPLC).

E. Bioconversion by Cell-free Extracts: Mycelia (4 g. wet weight) in phosphate buffer (pH 6.5) are blended in a Waring blender at low speed for 15 seconds. The buffered homogenate is then transferred to a 50 ml. glass Duran Sample Flask containing 50 g. (about 80% by volume) glass beads of a diameter of 0.45 to 0.5 mm. The chamber is then vigorously agitated with a Braun Mechanical Cell for 1 minute while cold carbon dioxide is allowed to flow past the chamber to minimize heating.

Alternatively, the low speed blended mycelia in buffer is placed in a plastic centrifuge tube in an ice bath and then sonicated with a Heat Systems Ultrasonics Cell Disrupter, Model 350, set at 50% duty cycle, output control at 6, continuous mode, in 5 cycles of 15 seconds on and 15 seconds off.

The samples are centrifuged at 9,000 rpm for 15 min., and the supernatant is carefully decanted into a *clean* test tube, discarding the pellet.

The supernatant is added to a column packed with Sephadex G-25 adsorbent by carefully pipetting the supernatant in a drop-wise manner onto the top of the bed of adsorbent in the column until the top of the bed is just covered with the liquid. Sufficient phosphate buffer is then carefully added to fill the area of the column above the bed.

As the column contents are slowly eluted through the column, a pale yellow band of extract can be seen passing down through the adsorbent. The effluent is discarded until the yellow extract begins to appear in the collection tube. Only the yellow extract portion is collected. At this point the extract collected is divided for protein assay and bioconversion.

Two concentrations of extracts, as described below, are evaluated in a total reaction mixture of 2 ml. In each case 4% glucose/phosphate buffer is used as the substrate.

Concentration A: 1 ml of extract is added to a test tube containing 0.5 ml 4% glucose/phosphate buffer and 0.5 ml phosphate buffer.

Concentration B: 1.5 ml of extract is added to a test tube containing 0.5 ml 4% glucose/phosphate buffer.

Each tube is then vortexed and immediately placed into a 30° C. water bath for 30 min. The mixture is then vortexed and incubated an additional 30 min. At the end of the incubation, samples were analyzed by HPLC.

II. Results

As shown by the following tabulation, 13 whole-cell bioconversions with *Polyporus obtusus* yielded an average of 5.4 mg glucosone per gram wet mycelia as against 13.9 mg glucosone per gram wet mycelia with the test fungus obtained from 21 runs. From total mycelia obtained in 100 ml of growth medium, *Polyporus obtusus* yielded 75.8 mg glucosone (average of 13 runs) as against 263.2 mg for the test fungus (21 runs). Similar results were obtained when the best 4 runs are compared for each culture.

The test fungus employed in these determinations has been deposited with the National Regional Research Laboratory where it has been accorded the accession number NRRL 15095.

Using the same methods and materials as previously described herein, further comparisons of *P. obtusus* with present new fungus species A and B, identified under NRRL numbers 15093 and 15094, were carried out and the results shown in the following table. The cell extract of *P. obtusus* was prepared from 2 g. wet mycelium ground in liquid nitrogen and 10 ml. of phosphate buffer at pH 6.5.

As the following table and the graph which comprises the sole FIGURE for this application show, the Polyporus extract derived from 1 g of mycelia produced about 0.5 g glucosone during the first 2 hrs. of incubation, while the whole cells of the two isolates produced only about 0.1–0.2 g glucosone/gram of mycelia. By the 6th hour, both the Polyporus extract and the 2 isolates produced about 0.8–0.9 g glucosone. By the 12th hour, the Polyporus extract gave 1.3 g glucosone, whereas the 2 isolates produced 2.3–2.5 g glucosone from 1 g of mycelia at this checkpoint. The attached graph shows that cultures A and B would produce more than 5.0 g glucosone per gram d.b. cell mass in 18–32 hours.

COMPARISON BETWEEN *POLYPORUS OBTUSUS* AND TEST FUNGUS

I. Bioconversion of glucose to glucosone with whole cells (HPLC Analysis)

| *Polyporus obtusus* | | | | TEST FUNGUS | | | |
|---|---|---|---|---|---|---|---|
| Bioconversion by 1 gm of mycelia | | Bioconversion by total mycelia obtained from 100 ml growth medium | | Bioconversion by 1 gm of mycelia | | Bioconversion by total mycelia obtained from 100 ml growth medium | |
| mg glucosone produced | μ mole glucosone produced | mg glucosone produced | μ mole glucosone produced | mg glucosone produced | μ mole glucosone produced | mg glucosone produced | μ mole glucosone produced |
| 5.76 | 32 | 12.4 | 69.7 | 20 | 112 | 425.6 | 2391.0 |
| 4.0 | 22 | 22.0 | 123.6 | 17.8 | 100 | 320.4 | 1800.0 |
| 11.0 | 64 | 125.4 | 704.5 | 25.8 | 145 | 193.6 | 1087.6 |
| 15.0 | 85 | 500.1 | 2809.6 | 13.5 | 76 | 108.0 | 606.0 |
| 11.8 | 66 | 122.7 | 689.3 | 24.0 | 135 | 323.8 | 1819.0 |
| 3.0 | 17 | 32.7 | 184.0 | 5.8 | 33 | 91.6 | 514.6 |
| 1.6 | 9 | 15 | 84.2 | 5.4 | 30 | 99.9 | 561.2 |
| 2.76 | 16 | 21.0 | 117.9 | 10.0 | 56 | 429.0 | 2410.0 |
| 1.7 | 9.6 | 12.4 | 69.7 | 12.6 | 71 | 367.9 | 2066.8 |
| 2.5 | 14.0 | 20.3 | 114.0 | 11.6 | 65 | 212.4 | 1193.3 |

II. Bioconversion of glucose to glucosone with whole cells (HPLC analyses)

| | | *Polyporus obtusus* | | | Test Fungus | | |
|---|---|---|---|---|---|---|---|
| Bioconversion Conditions | Analytical Method | mg glucosone per gram mycelia | μ mole glucosone produced per gram mycelia | mg glucosone produced per total mycelia from 100 ml medium (12 grams) | Mg glucosone per gram mycelia | μ mole glucosone produced per gram mycelia | mg glucsone produced per total mycelia from 100 ml medium (35.2 grams) |
| 0.5 grams mycelia incubated at 35° C. in test tubes for 16 hours with 5 ml 6% glucose substrate containing 0.02M NaF | HPLC | 7.96 | 44.7 | 95.5 | 8.55 | 48.0 | 300.9 |
| | HPLC | 4.62 | 26.3 | 40.4 | 29.0 | 162.9 | 862.9 |

| *Polyporus obtusus* | | Test Fungus | |
|---|---|---|---|
| Bioconversion by 1 gm of mycelia | Bioconversion by total mycelia obtained from 100 ml growth medium | Bioconversion by 1 gm of mycelia | Bioconversion by total mycelia obtained from 100 ml growth medium |
| μ mole | μ mole | μ mole | μ mole |

-continued

COMPARISON BETWEEN POLYPORUS OBTUSUS AND TEST FUNGUS

| mg glucosone produced | glucosone produced | mg glucosone produced | glucosone produced | mg glucosone produced | glucosone produced | mg glucosone produced | glucosone produced |
|---|---|---|---|---|---|---|---|
| | | | | 15.8 | 89 | 276.4 | 1552.9 |
| 0.5 | 2.8 | 2.3 | 12.9 | 18.4 | 103 | 284.8 | 1600.0 |
| 0.6 | 3.4 | 2.2 | 12.3 | 14.2 | 80 | 284.4 | 1597.7 |
| 9.4 | 52.8 | 96.8 | 543.8 | 13.2 | 74 | 256.1 | 1438.8 |
| | | | | 15.0 | 84 | 364.5 | 2047.8 |
| | | | | 8.5 | 47.8 | 225.3 | 1265.7 |
| | | | | 12.5 | 70.2 | 308.8 | 1734.8 |
| | | | | 13.2 | 74.1 | 256.1 | 1438.8 |
| | | | | 15.0 | 84.3 | 364.5 | 2047.7 |
| | | | | 8.5 | 47.8 | 225.3 | 1265.7 |
| | | | | 12.5 | 70.2 | 308.8 | 1734.8 |
| General Average | | | | | | | |
| 5.4 | 30.3 | 75.8 | 425.8 | 13.96 | 78.4 | 263.2 | 1478.7 |
| Average of best four runs | | | | | | | |
| 11.9 | 66.9 | 211.3 | 1186.8 | 21.9 | 123.0 | 315.8 | 1774.4 |

TABLE NO. 1

| Culture No. | Gram Glucosone/Gram d.b. Cell | | | | | | | | | | | | |
|---|---|---|---|---|---|---|---|---|---|---|---|---|---|
| | 0 Hr. | 2 Hr. | 4 Hr. | 6 Hr. | 8 Hr. | 10 Hr. | 12 Hr. | 14 Hr. | 16 Hr. | 18 Hr. | 20 Hr. | 25 Hr. | 32 Hr. |
| Control Polyporous (Extract) | 0.01 | 0.50 | 0.79 | 0.86 | 1.12 | 0.96 | 1.29 | — | — | — | — | 0.82 | — |
| SAMPLE A (Whole Cell) Run No. 1 | 0.00 | 0.18 | 0.52 | 0.93 | 1.44 | 1.59 | 2.50 | — | — | — | — | 0.96 | — |
| SAMPLE A (Whole Cell) Run No. 2 | — | — | — | — | 1.65 | 2.23 | 2.47 | 2.69 | 2.99 | 3.36 | 3.79 | — | 5.06 |
| SAMPLE B (Whole Cell) Run No. 1 | 0.00 | 0.12 | 0.48 | 0.81 | 1.24 | 1.71 | 2.32 | — | — | — | — | 5.37 | — |
| SAMPLE B (Whole Cell) Run No. 2 | — | — | — | — | 1.67 | 2.60 | 2.89 | 3.12 | 3.82 | 5.73 | — | — | 5.77 |

We claim:

1. A process for producing glucosone and co-producing hydrogen peroxide which comprises contacting an aqueous solution of glucose with oxygen and glucose-2-oxidase produced by at least one fungus of the Basidiomycetes class selected from the group consisting of NRRL 15093, NRRL 15094 and NRRL 15095, said fungus being characterized in that substantially all of the glucose-2-oxidase activity thereof is available to aqueous glucose substrate on contact therewith without disruption of the fungus.

2. The process according to claim 1 wherein mycelia of said fungus are contacted with said aqueous glucose solution.

3. The process of claim 1 wherein the co-produced hydrogen peroxide is destroyed, utilized or removed from the reaction mixture when produced.

4. The process of claim 3 wherein the co-produced hydrogen peroxide is catalytically decomposed to water and oxygen.

5. The process of claim 3 wherein the co-produced hydrogen peroxide is decomposed by enzymes in the fungus mycelia.

6. The process of claim 3 wherein the co-produced hydrogen peroxide is reacted with an olefin to form an oxygenated product.

7. The process of claim 1 wherein the glucosone product is enzymatically converted to 2-ketogluconic acid by contact with glucose-1-oxidase.

8. The process of claim 1 wherein the glucosone product is catalytically hydrogenated to fructose.

* * * * *